United States Patent [19]

Srinivasan et al.

[11] Patent Number: 4,713,336

[45] Date of Patent: Dec. 15, 1987

[54] GENE FOR LIGNIN DEGRADATION AND USES THEREOF

[75] Inventors: Vadake R. Srinivasan; Jeffrey W. Cary; Younghae Chon; Kenneth E. Narva, all of Baton Rouge, La.

[73] Assignee: Research Corporation Technologies, Inc., Tucson, Ariz.

[21] Appl. No.: 655,193

[22] Filed: Sep. 27, 1984

[51] Int. Cl.[4] .......................... C12P 7/02; C12N 9/14; C12N 15/00; C07H 15/12

[52] U.S. Cl. ........................................ 435/155; 435/68; 435/172.3; 435/172.1; 435/195; 435/253; 435/847; 435/319; 536/27; 935/14; 935/29; 935/56; 935/60; 935/72

[58] Field of Search ................ 435/155, 172.3, 195, 435/253, 317, 847, 172.1; 536/27; 935/14, 29, 56, 60, 72

[56] References Cited

FOREIGN PATENT DOCUMENTS

WO84/00001-75  1/1984  PCT Int'l Appl. .............. 435/172.3

OTHER PUBLICATIONS

Tien et al, *Proc Natl Acad Sci*, vol. 81, pp. 2280–2287, Apr. 1984, "Lignin-Degrading Enzyme from Phanerochaetic Catalytic Properties of a Unique $H_2O_2$ Requiring Oxygenide".

Setliff et al, *Chem Abst*, vol. 93, No. 146013y, 1978, "Screening White-Rot Fungi Further Capacity to Delignify Wood".

Neborachko, *Chem Abst*, vol. 97, No. 12133x, 1982, "Cloning *Erwinia Carotovora* DNA in *E coli* Cells.

Wang et al, *Cheml Abst*, vol. 89, No. 734020d, 1978, "Erwihia Salicis in Cricket Bat Willows: Histology and Histochemistry of Infected Wood".

*Primary Examiner*—Thomas G. Wiseman
*Assistant Examiner*—Robin Lyn Teskin
*Attorney, Agent, or Firm*—Scully, Scott, Murphy & Presser

[57] ABSTRACT

This invention relates to the field of lignin degradation. More specifically the invention relates to methods for selecting and isolating microorganism from nature that are capable of degrading lignin, processes for cloning a gene segment from such an organism, and methods of using the enzyme product of the gene segment to provide valuable chemical feedstocks, methanol and the like from a lignin source material.

22 Claims, 5 Drawing Figures

PNPG

Salicin

Vanillin

Vanillic acid

Catechol

Syringaldehyde

Syringic acid p-Phenoxy phenol lignin 1  2  3  4

L.0hr  2   4   8   20  L.st20  C  L.st

GENE FOR LIGNIN DEGRADATION AND USES THEREOF

FIELD OF THE INVENTION

This invention relates to the field of lignin degradation. More specifically the invention relates to methods for selecting and isolating microorganisms from nature that are capable of degrading lignin, processes for cloning a gene segment from such an organism, and methods of using the enzyme product of the gene segment to provide valuable chemical feedstocks, methanol and the like from a lignin source material.

BACKGROUND OF THE INVENTION

Lignin is an abundant phenolic biopolymer, comprising approximately one quarter of the weight of dry wood. The structure of lignin is quite complex and insights into its structure have only recently been elucidated. As contrasted with other biopolymers such as starch, cellulose, proteins, nucleic acids and the like, lignin does not possess any repeating units nor are its chemical bonds particularly easy to hydrolyze. Ether bonds are often prevalent, providing a variety of linkages to the numerous aromatic residues. A portion of a typical structure is illustrated in FIG. 1.

Lignin is synthesized non-enzymatically by the coupling of three types of phenylpropane units (coumarylalcohol, coniferylalcohol, and sinapylalcohol) to form dilignols, trilignols and oligolignols which continue to couple in a random fashion with each other and additional monomer units. The lignin product is a copolycondensate, insoluble in water and possessing a molecular weight of tens of thousands.

Although generally resistant to microbial attack, lignin degradation has been demonstrated among members of litter-decomposing fungi, most notably the so-called white-rot fungi. One particular species, *Phanerochaete chrysosporium*, has been the focus of a good deal of research (See for example: D. Ulmer et al., Eur. J. Appl. Microbiol. Biotechnol. 18: 153-157 (1983) and M. Leisola, et al. Arch. of Microbiol 137: 171-175 (1984)). Additionally, lignin degradation has been shown to occur by the action of certain strains of *Streptomyces spp.* (T. Pettey et al., Appl. Environ. Microbiol. 47 (2): 439-440 (1984)) as well as by a bacterium tentatively identified as belonging to the genus Arthrobacter isolated from decaying peanut hulls (T. Kerr et al. Appl. Environ. Microbiol. 46 (5): 1201-1206 (1983)).

Recently, $^{13}$CNMR techniques have provided some insights as to mechanism of lignin degradation by white-rot fungi (M. Chua et al. Holzforschung 36: 165-172 (1982)). These studies indicate that aromatic nuclei integrated in the polymer are oxidatively cleaved with the aromatic moieties being further degraded to aliphatic structures.

It is desirable to identify new microbial strains capable of degrading lignin for use in the manufacture of cellulosic products from lignocellulose by "biological pulping" as described in U.S. Pat. No. 3,962,033, the treatment of lignin-derived waste such as the Kraft black plant effluent (Kirk, T. et al., Biotechnol. Lett. 1: 347-352 (1979)), or the production of food or fuel (Lindenfelser, L. et al. Dev. Ind. Microbiol. 20: 541-551 (1979)). It is also desirable to isolate microorganisms capable of partial degradation of lignin in order to provide a source of valuable chemical feedstocks for the production of fine chemicals.

BRIEF DESCRIPTION OF THE INVENTION

This invention provides a biologically pure culture of a lignin-degrading microorganism of the genus Erwinia having the identifying characteristics of ATCC 39873.

In a further embodiment this invention provides a method for the isolation of lignin degrading microorganisms from a sample containing lignin-degrading and lignin non-degrading microorganisms comprising:

enriching the sample for lignin-degrading microorganism by incubating the sample in an enriching medium comprising methanol at an alkaline pH;

incubating the enriched sample in a selection medium comprising yeast extract lignin as a carbon source at an alkaline pH;

isolating lignin-degrading microorganism by recovering those microorganisms capable of forming colonies on a solid medium.

In yet a further embodiment this invention provides a DNA segment coding for an aryl etherase protein or its single or multiple base substitutions, deletions, insertions or inversions, wherein said DNA segment is derived from a lignin-degrading microorganism, and is capable, when correctly combined with a cleaved vector, of expressing a non-native protein having aryl etherase enzyme activity upon transformation of a host by said vector.

In yet a further embodiment this invention provides a vector comprising a DNA segment which codes for an aryl etherase protein, the segment being oriented within said vector such that in a host said segment is expressed to produce a non-native aryl etherase protein.

In yet a further embodiment this invention provides a host organism organism transformed by a vector comprising a DNA segment which codes for an aryl etherase protein.

In yet a further embodiment this invention provides a process for the degradation of lignin comprising contacting a sample of the lignin to be degraded under lignin-degrading conditions with a host organism transformed by a vector comprising a DNA segment which codes for an aryl etherase protein, the segment being oriented within said vector such that said segment is expressed to produce said aryl etherase.

In yet a further embodiment this invention provides a process for producing methanol from lignin comprising culturing a host organism transformed with a vector comprising a DNA segment which codes for an aryl etherase protein said segment being oriented within said vector such that said segment is expressed to produce said aryl etherase, under methanol forming culture conditions.

In a final embodiment this invention provides a process for the production of chemical feed stocks from lignin comprising culturing a host organism transformed with a vector comprising a DNA segment which codes for an aryl etherase protein, said segment being oriented within said vector such that said segment is expressed to produce said aryl etherase, under chemical feedstock forming conditions.

DETAILED DESCRIPTION OF THE DRAWINGS

Figure 3:
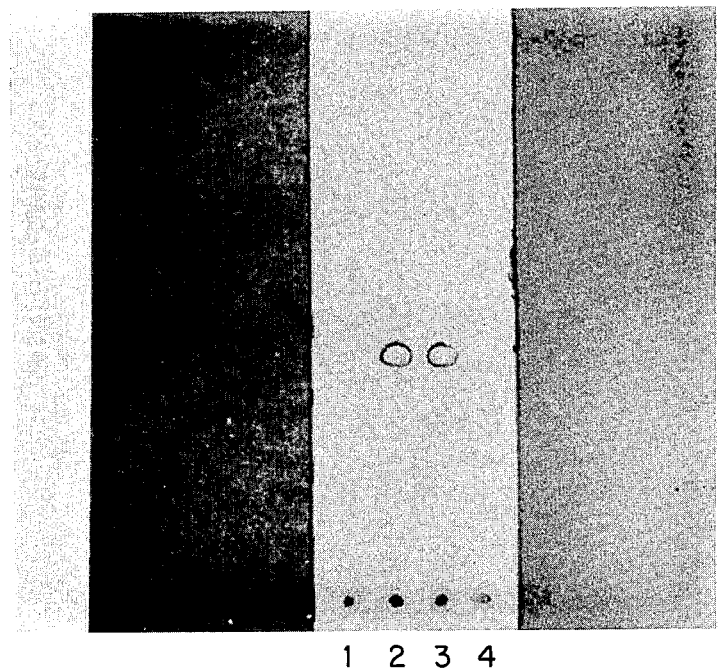

FIG. 3 demonstrates the activity of the cloned aryletherase on Kraft lignin as analyzed by thin layer chromatography. Lane 1, *E. coli* Cs412 (control); lane 2, Cs412 pNCl transformant: lane 3, Cs412 pNC2 transformant; lane 4, Kraft lignin standard.

Figure 4:
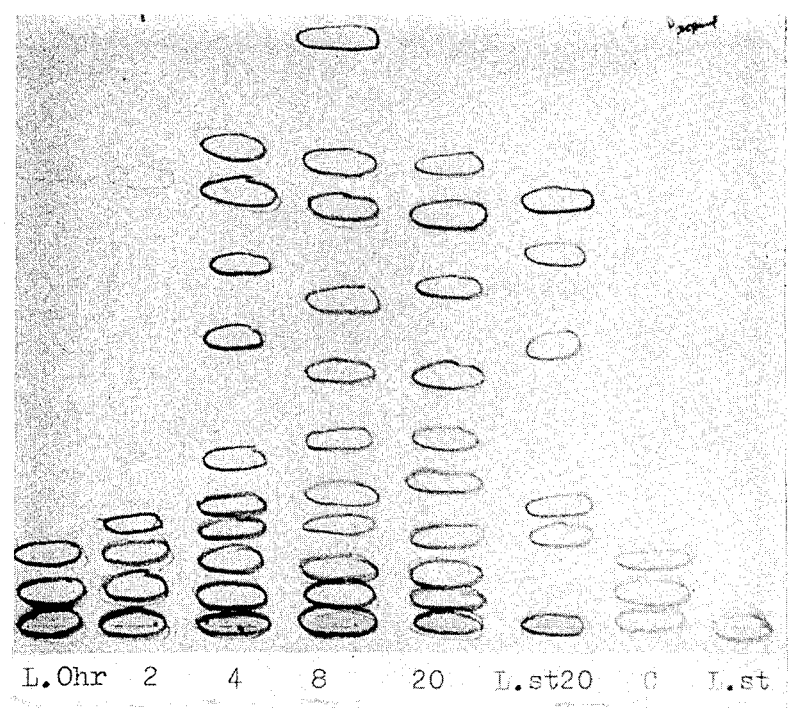

FIG. 4 illustrates the separation of lignin metabolites after 2, 4, 8, and 20 hrs of incubation with the isolated bacterium by thin layer chromatography. Solvent: Benzene, 2-propanol, NH$_4$OH (4:1:1). L=lignin, C=control (cells incubated for 20 hrs), L.st(20)=lignin incubated with the boiled cells for 20 hrs, L.st=lignin standard. Products were detected under a short-wave ultraviolet lamp (UVS.12, Ultraviolet Products INC.).

DETAILED DESCRIPTION OF THE INVENTION

Lignin has great potential as a renewable resource for the production of chemical feedstocks; however, it is relatively resistant to microbial degradation. Lignin also represents a major component of the spent sulfite and Kraft black liquors of the pulp and paper industry. Investigations involved with biodegradation of lignin are of economic ecological importance in the development of efficient bioconversion processes of this seemingly recalcitrant heteropolymer.

As mentioned previously, a variety of microorganisms have been shown to degrade lignin and lignin related model compounds. Recently, Kirk and Tien, (*Proc. Nat'l. Acad. Sci. USA* 81: 2280–84 (1984)) isolated and purified an enzyme to able to depolymerize lignin from the white-rot fungus *Phanerochaete chrysosporium*.

This invention provides methods for the isolation of a lignin-degrading microorganisms and the cloning of a gene encoding an enzyme capable of breaking arylether linkages into *E. coli* plasmid pBR322. The cloned aryletherase degrades lignin from Kraft black liquor and also several lignin model compounds.

Selection of Lignin Degrading Microbes

In one of its embodiments this invention provides a method for the selection of lignin-degrading microorganisms. Historically, two basic methods for recovery of desirable microbial variants have been employed, screening and selection.

In a screening system, all strains grow with the exception of those killed outright, as would result, for example, from a mutagenesis treatment; thus each isolate must be examined individually to identify the desired characteristic. Since tens of millions of isolates must be examined, this approach can be highly labor intensive. This is particularly true if the characteristic is an intracellular one. In such a situation since the cells must be disrupted in order to identify the desired characteristic, back-up cultures of each isolate must be maintained, necessitating at least twice the number of cultures.

In a selection system, the experimental conditions are chosen so as to establish a growth differential between the rare strains possessing the desired characteristic and all other strains which do not possess said trait. In certain instances the selected strain will not grow under the conditions of the experiment while the non-selected strains will grow. Thus by removing the growing strains, by filtration or other means, the size of the remaining population of cells to be examined is dramatically reduced. Alternatively, conditions may be established such that the selected strain will grow while the non-selected strains are inhibited, here again effectively reducing the population to be examined and enriching the remaining population with the variant of interest.

It is readily apparent that a useful selection system is based on an appreciation of the relationship of the selective agent and the nature of the microorganism to be isolated. The enrichment system of this invention is predicated on the realization that methanol would likely be a degradation product of lignin metabolism and hence microbes capable of lignin degradation would likely be tolerant to the presence of methanol. Further, the ability of lignin degraders to use lignin as a carbon source provides a further rational basis for the selection system employed herein.

Although as described in detail herein, the selection scheme was used to isolate a lignin degrading microorganism from nature, the method is useful for selection regardless of the source of the variant strain. The strain may be naturally occurring, an induced mutation, or a recombinant resulting from sexual, asexual or genetic engineering processes. The method of selection described herein is particularly useful in permitting the experimentor to recover the desired variant strain from among the population of non-lignin degrading strains from which it arose.

A particularly useful lignin-degrading bacterium, tentatively identified as a saprophytic Erwinia sp., was isolated from sewage.

The sample was first enriched for potential lignin degrades by culturing in a medium comprising methanol between about 0.2% and about 5% v/v, with about 1% being preferred. Since many lignin-degrading strains have been shown to be alkalophilic, it is preferred to carry out the enrichment at an alkaline pH; a pH of about 9 is useful. After enrichment for 2–3 days at a temperature between 30°–37° C. in the presence of 1% methanol, the sample was subjected to a selection procedure whereby the enriched sample was cultured for 2–3 days on a medium comprising minimal salts, (as described by R. Summers et al. (*Appl. Environ. Microbiol.* 38 (1): 66–71 (1979)), yeast extract, and Kraft lignin at pH 9.0. Following a series of transfers through a medium comprising glucose, a prototroph able to grow on lignin as the sole carbon source was recovered. As mentioned above, one such isolate has been tentatively identified as Erwinia sp.. The metabolic products resulting from the incubation of this isolate with lignin were resolved by the layer chromatography (FIG. 4). The sample of the culture has been deposited with the American Type Culture Collection and has been assigned the accession number 39873.

Aryletherase Characterization

The ability of the organism to grow in the presence of methanol and utilize lignin as a carbon source suggested that aromatic etherases may be responsible for lignin degradation. p-Nitrophenyl-β-D-glucopyranoside (PNPG, FIG. 1) which possess a pseudoether linkage between the aromatic nucleus and the sugar moiety, was used as a chromogenic substrate to assay the presence of aryletherase activity in the isolate. Incubation of cell cultures (or partially purified enzyme) with PNPG released yellow p-nitrophenol. Since the organism is unable to utilize cellobiose or lactose as carbon sources, the enzyme responsible for PNPG cleavage is presumably not a β-glucosidase or β-galactosidase. Furthermore, 5-bromo-4-chloro-3-indolyl-β-D-galactoside (x-gal) and the β-D-glucoside derivative (x-glu) both showed release of the blue indolyl moeity when added to cell cultures. These results indicate that the specificity of the enzyme lies in the recognition of the aromatic component of the substrates employed.

The enzyme was partially purified from sonicated cell-free extracts by polyethylenimine treatment, ammonium sulfate fractionation, and DEAE cellulose ion exchange chromatography resulting in a 33% yield. The enzyme is active over a wide pH range (4.5–9.5), with an optimum of pH 6.0–7.0. Heat inactivation studies showed that enzyme activity was readily lost at temperature above 50° C.

Cloning of the Aryletherase Gene

In order to clone the aryletherase gene Bam HI digested Erwinia DNA was ligated into the Bam HI site of pBR322 and used to transform *E. coli* strain Cs412 (McLaughlin, J. R., et al., *Nucleic Acid Res* 10: 3905–3919 (1982)) by the methods of Hanahan (*J. Mol. Biol.* 166: 447–580 (1983)). Transformants were plated on M9 minimal medium (Maniatis, T. et al. In: "Molecular Cloning" Cold Spring Harbor Laboratory pp. 68–69 (1982)) containing salicin as sole carbon source and ampicillin (40 μg/ml) as the other selective agent. Salicin (FIG. 1), which contains a pseudoether linkage between glucose and an aromatic nucleus, supported the growth of the Erwinia isolate but not the *E. coli* host strain Cs412. Of the several hundred transformants obtained, 30 were examined for aryletherase activity using PNPG as the chromogenic substrate. Three isolates were obtained with the capability of releasing yellow p-nitrophenol from PNPG. The recombinant plasmids from 2 of the isolates (pNC1 and pNC2) conferred the ability to utilize salicin to *E. coli* Cs412 in subsequent transformation studies.

Figure 2A:
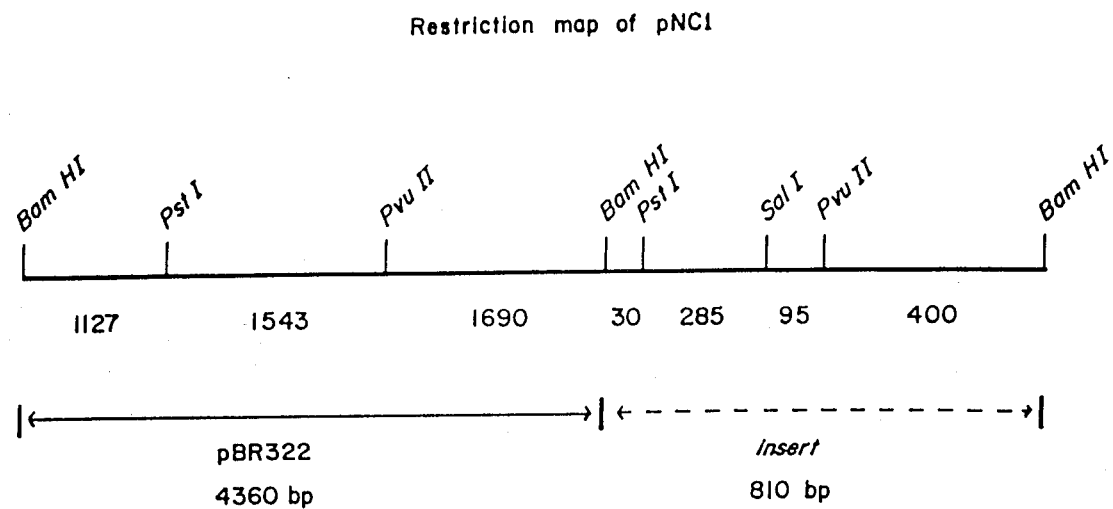
FIG. 2a illustrates the restriction map of plasmid pNCl.
Figure 2B:
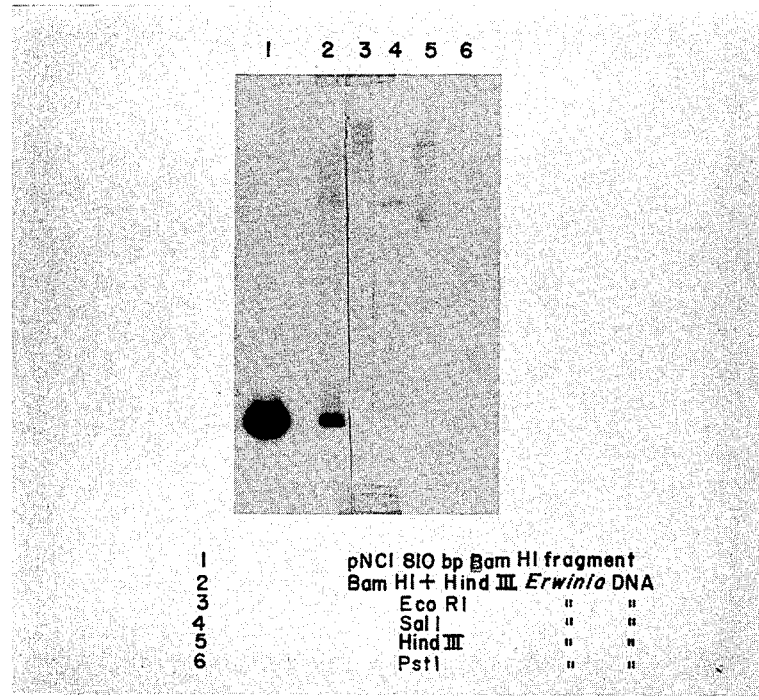
FIG. 2b illustrates the hybridization of Erwinia genomic DNA with $^{32}$P-labelled probe DNA from pNCl. Lane 1, pNCl 810 bp Bam HI fragment (0.1 μg); lanes 2–6, Erwinia DNA digested with Bam HI+Hind III, EcoRI, Sal I, Hind III, Pst I respectively.

Plasmid pNC1 was shown to contain an 810 bp DNA insert upon digestion with Bam HI. The results of further restriction endonuclease mapping are shown in FIG. 2a. The insert contains single restriction sites for Sal I, Pst I, and Pvu II but no internal sites for EcoRI, Hind III, Ava I, or Cla I. $^{32}$P-Nick translated (Rigby, P. W. J et al. *J. Mol. Biol.* 113: 237–251 (1977)) pNC1 was used as a probe to demonstrate sequence homology between the cloned gene and Erwinia genomic DNA (Southern, E. M., *J. Mol. Biol.* 98: 503–517 (1975)). Genomic DNA (5 ug) isolated by the method of Saito and Mivra (*Biochem. Biophys. Acta.* 72: 619–269 (1963)) was digested to completion with 40 U each of the various restriction endonucleases (BRL), electrophoresed on 0.8% agarose gel, and transferred to a nitrocellulose filter. $^{32}$P-labelled pNC1 was prepared and $10^6$ cpm of the probe was hybridized with the filter in 50% formamide, 4×ssc, 1×Denhardt's solution containing 20 ug/ml sonicated, denatured calf thymus DNA for 24 hrs at 42° C. The filter was then washed 3 times in one hour with 1×ssc, 0.1% SDS and then twice in one hour with 1×ssc, 0.1% SDS before exposure to X-ray film. Since no internal Hind III sites are present in the gene, Erwinia genomic DNA was digested with Hind III and Bam HI before agarose gel electrophoresis to enhance the signal obtained (FIG. 2b, lane 3). A single Bam HI fragment migrating with the same mobility as the 810 bp fragment containing the aryletherase gene was observed. The probe also showed homology with single Hind III and Pst I fragments and with two Sal I fragments. On examining the restriction map of the aryletherase gene, these results suggest the gene is present as a single copy on the Erwinia sp. chromosome.

Expression of Cloned Aryletherase in *E. coli*

Lignin and several model compounds were degraded by the isolate as demonstrated by thin layer chromatography (TLC) after incubation with whole cells. Complete degradation of vanillin after initial oxidation to vanillic acid suggests that the Erwinia isolate produces several enzymes such as hydroxylase and oxygenase which are involved in aromatic ring fission processes.

Figure 1:
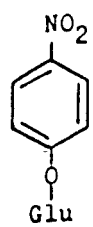
FIG. 1 illustrates the molecular structures of various compounds referred to in the specification.
Figure 1:
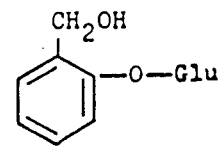
Figure 1:
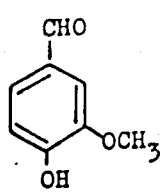
Figure 1:
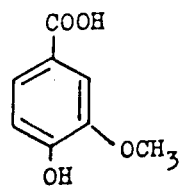
Figure 1:
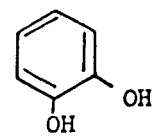
Figure 1:
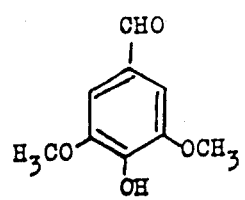
Figure 1:
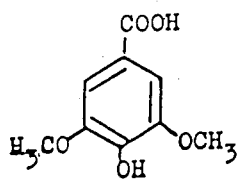
Figure 1:
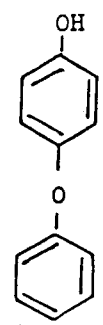
Figure 1:
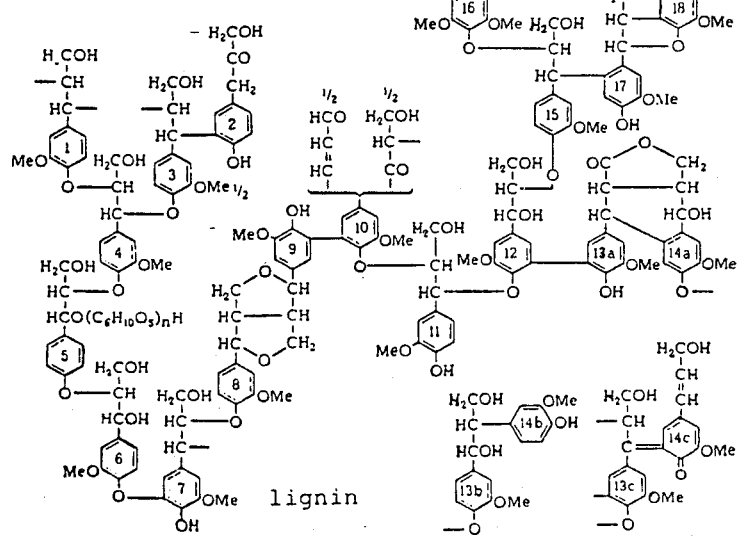

Cloning of the aryletherase gene into pBR322 allowed its study in the absence of the other enzymes which resulted in ring fission. The aryletherase was expressed in *E. coli* Cs412 and the transformants produced a single, unidentified aromatic compound in 2 hours incubation time with lignin (FIG. 3). Cells of *E. coli* Cs412 or those transformed with pNC1 or pNC2 were grown in 10 ml batch culture, pelleted at 12,000×g, and resuspended in 1 ml 0.1% Kraft lignin in 10 mM MgCl$_2$, 10 mM Tris HCl pH 7.8. Incubation was at 32° C. for 2 hours. Solvent system was benzene, 2-propanol, HH$_4$OH (4:1:1). Product and standard were detected with short-wave ultraviolet light. The possibility exists that there may be other lignin degradation products not resolved in the solvent system employed. Vanillin and vanillic acid were demethylated to catechol after incubation with transformed strains. Catechol was identified by TLC after comparison with standards in several solvent systems. TLC analysis also showed that the cloned aryletherase was able to degrade p-phenoxyphenol, syringaldehyde, and syringic acid (FIG. 1). The product of p-phenoxyphenol degradation was identified as hydroxyquinone by TLC. NMR analysis of the product showed it to be p-benzoquinone, which probably results from oxidation of hydroxyquinone.

The results presented show that the cloned aryl etherase is capable of cleaving arylether linkages as well as methoxyl groups in aromatic lignin model compounds. As is common in the enzyme art, an enzyme is often referred to by a variety of names, each reflecting a particular substrate specificity of that enzyme. In the instant case, although the term aryl etherase is preferred; the enzyme may be referred to as a demethylase, demethoxylase, aryl, alkyl ether hydrolase, or diaryl etherase each indicating a functional property of the enzyme.

A deposit of biologically pure culture of the bacterium capable of degrading lignin tentatively identified as Erwinia sp. and a deposit of the plasmid pNC1 containing the cloned aryletherase gene transformed into *E. coli* were made with the American Type Culture Collection, 12301 Parklawn Drive, Rockville, Maryland on Sept. 20, 1984, the accession numbers ATCC 39873 and ATCC 39874 respectively were assigned and the requisite fees were paid. Access to said cultures will be available during pendency of this patent application to one determined by the Commissioner to be entitled thereto under 37 C.F.R. §1.14 and 35 U.S.C. §122. All restriction on availability of said culture to the public will be irrevocably removed upon the granting of a patent based upon this application and said cultures will remain permanently available during the term of said patent; and should the cultures become nonviable or be inadvertently destroyed, they will be replaced with viable cultures of the same taxonomic description.

A host organism transformed by a vector containing an expressible aryl etherase gene is particularly useful for the production of the aryl etherase protein product. Alternatively, the transformed host under appropriate lignin-degrading conditions, can be used in a lignin-degrading process. Furthermore, the aryl etherase may be isolated from the host and used in immobilized or free form as lignin-degrading catalyst. Finally, the transformed host can be used in processes for methanol production as well as chemical feedstock production.

What is claimed is:

1. A biologically pure culture of a lignin degrading microorganism of the genus Erwinia having all the identifying characteristics of ATCC 39873 and mutants thereof.

2. A vector comprising a DNA segment which codes for an aryl etherase protein, the segment being oriented within said vector such that in a host said segment is expressed to produce a non-native aryl etherase protein said segment being derived from a microorganism having all the identifying characteristic of ATCC 39873 or mutants thereof.

3. The vector according to claim 2 wherein said host is *E. coli*.

4. The vector according to claim 2 wherein said vector is a plasmid.

5. The vector according to claim 4 wherein said plasmid is pBR322.

6. The vector according to claim 2 wherein said DNA segment is about 810 base pairs in length, the termini of said segment being Bam H1 restriction sites, and said segment comprising internal restriction sites for Sal I, Pst I, adn Pvu II.

7. The vector according to claim 2 wherein said vector is pNC1.

8. A bacterial host organism transformed by the vector of claim 2.

9. The host according to claim 8 wherein said host is *E. coli*.

10. The host according to claim 9 wherein said *E. coli* is strain Cs412.

11. The host according to claim 10 wherein said host has all the identifying characteristics of ATCC 39874 or mutants thereof.

12. A process for producing aryl etherase which comprises culturing a bacterial host transformed with a vector comprising a DNA segment which codes for an aryl etherase protein, the segment being oriented within said vector such that in a host said segment is expressed to produce a non-native aryl etherase protein said segment being derived from a microorganism having all the identifying characteristics of ATCC 39873 or mutants thereof.

13. A process for producing aryl etherase according to claim 12 wherein said host has all the identifying characteristics of ATCC 39874 or mutants thereof.

14. A process for the degradation of lignin comprising contacting a sample of the lignin to be degraded under lignin degrading conditions with a host organism transformed by a vector comprising a DNA segment which codes for an aryl etherase protein, wherein the aryl etherase protein has all the identifying characteristics of the aryl etherase protein produced by Erwinia ATCC 39873 or mutants thereof which retain lignin degrading activity, the segment being oriented within said vector such that said segment is expressed to produce said aryl etherase.

15. The process of claim 14 wherein said host has all the identifying characteristics of ATCC 39874 or mutants thereof.

16. The process according to claim 15 wherein said host is immobilized.

17. A process for producing methanol from lignin comprising culturing in the presence of lignin under methanol forming culture conditions, a host organism transformed with a vector comprising a DNA segment which codes for an aryl etherase protein, wherein the aryl etherase protein has all the identifying characteristics of the aryl etherase protein produced by Erwinia ATCC 39873 or mutants thereof which retain lignin degrading activity, said segment being oriented within said vector such that said segment is expressed to produce said aryl etherase.

18. The process according to claim 17 wherein said host has all the identifying characteristic of ATCC 39874 or mutants thereof.

19. The process for the production of chemical feedstocks from lignin comprising culturing in the presence of lignin a host organism transformed with a vector comprising a DNA segment which codes for an aryl etherase protein, wherein the aryl etherase protein has all the identifying characteristics of the aryl etherase protein produced by Erwinia ATCC 39873 or mutants thereof which retain lignin degrading activity, said segment being oriented within said vector such that said segment is expressed to produce aryl etherase, under chemical feedstock forming conditions.

20. The process according to claim 19 wherein said host is ATCC 39874.

21. A process for the degradation of lignin comprising contacting a sample of the lignin to be degraded under lignin degrading conditions with an aryl etherase extracted from a host organism transformed by a vector comprising a DNA segment which codes for an aryl etherase protein having all the identifying characteristics of the aryl etherase protein produced by Erwinia ATCC 39873 or mutants thereof which retain lignin degrading activity, the segment being oriented within said vector such that said segment is expressed to produce said aryl etherase.

22. The process according to claim 21 wherein said aryl etherase is immobilized.

* * * * *